United States Patent [19]

Bonner, Jr.

[11] Patent Number: 4,556,055
[45] Date of Patent: Dec. 3, 1985

[54] COLD COMPRESS

[76] Inventor: Francis J. Bonner, Jr., 136 Biddulph Rd., Radnor, Pa. 19087

[21] Appl. No.: 665,265

[22] Filed: Oct. 26, 1984

[51] Int. Cl.$^4$ ................................................. A61F 7/02
[52] U.S. Cl. .................................. 128/82.1; 62/259.3; 128/155; 128/402; 128/DIG. 15
[58] Field of Search ................ 128/82, 82.1, 155, 156, 128/157, 165, 402, 403, DIG. 15, 399, 384; 62/530, 259.3

[56] References Cited

U.S. PATENT DOCUMENTS

| | | | |
|---|---|---|---|
| 1,491,539 | 4/1924 | Kirschmann | 128/402 |
| 2,577,945 | 12/1951 | Atherton | 128/156 |
| 2,756,746 | 7/1956 | Munrett | 128/402 X |
| 3,935,858 | 2/1976 | Harroff | 128/165 X |
| 4,036,220 | 7/1977 | Bellasalma | 128/82 |
| 4,081,150 | 3/1978 | Tyson | 128/402 |
| 4,092,982 | 6/1978 | Salem | 128/402 |
| 4,344,303 | 8/1982 | Kelly, Jr. | 62/530 |

FOREIGN PATENT DOCUMENTS

| | | |
|---|---|---|
| 6900095 | 12/1968 | Fed. Rep. of Germany . |
| 958142 | 5/1964 | United Kingdom . |
| 960864 | 6/1964 | United Kingdom . |
| 1020083 | 2/1966 | United Kingdom . |

Primary Examiner—Anton O. Oechsle
Attorney, Agent, or Firm—Seidel, Gondas,. Goldhammer & Abbott

[57] ABSTRACT

A bandage is defined by a layer of closed cell foam polymeric material sandwiched between and bonded to adjacent layers of fabric. One of the layers of fabric is absorbent with respect to aqueous liquids and is adapted to be in contact with an area of the body. A plurality of straps are releasably attached to the bandage to form a compress. The straps facilitate adjustment of the compress. Optionally, a plurality of elongated pockets may be sewn to the fabric layer opposite the absorbent layer for insertion of straps to form a brace or provide for additional cooling. Electrodes may be incorporated into the bandage to provide electrical stimulation.

12 Claims, 4 Drawing Figures

U.S. Patent    Dec. 3, 1985    4,556,055
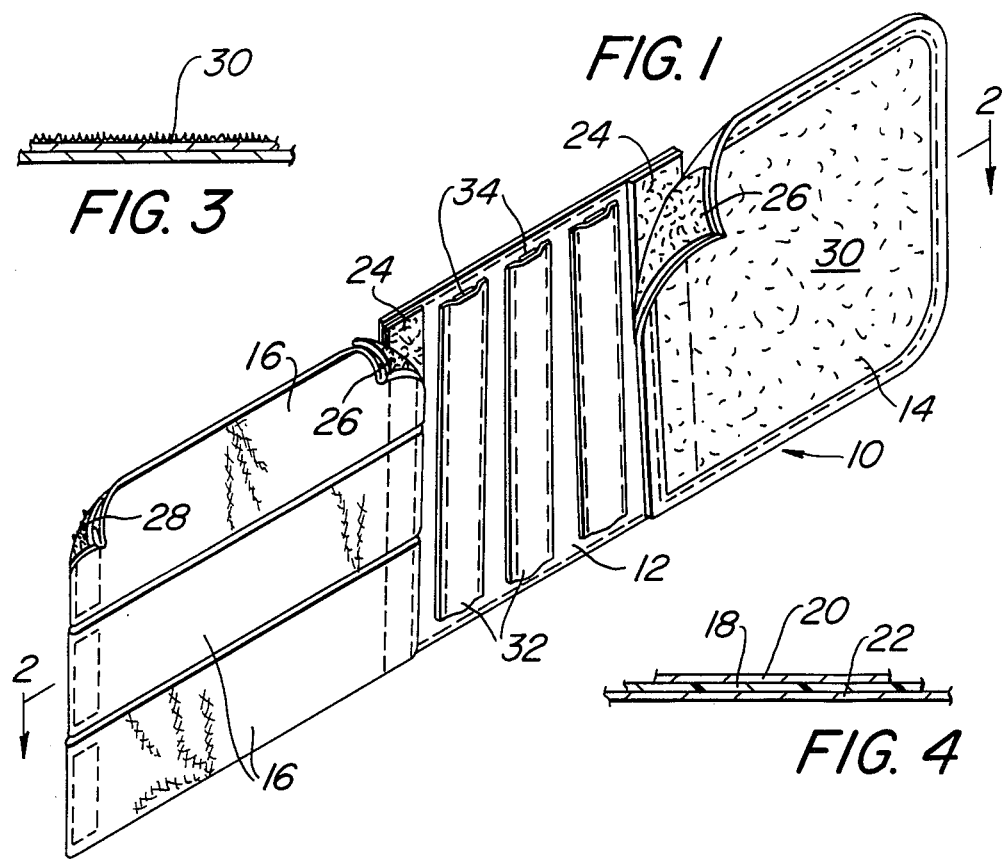
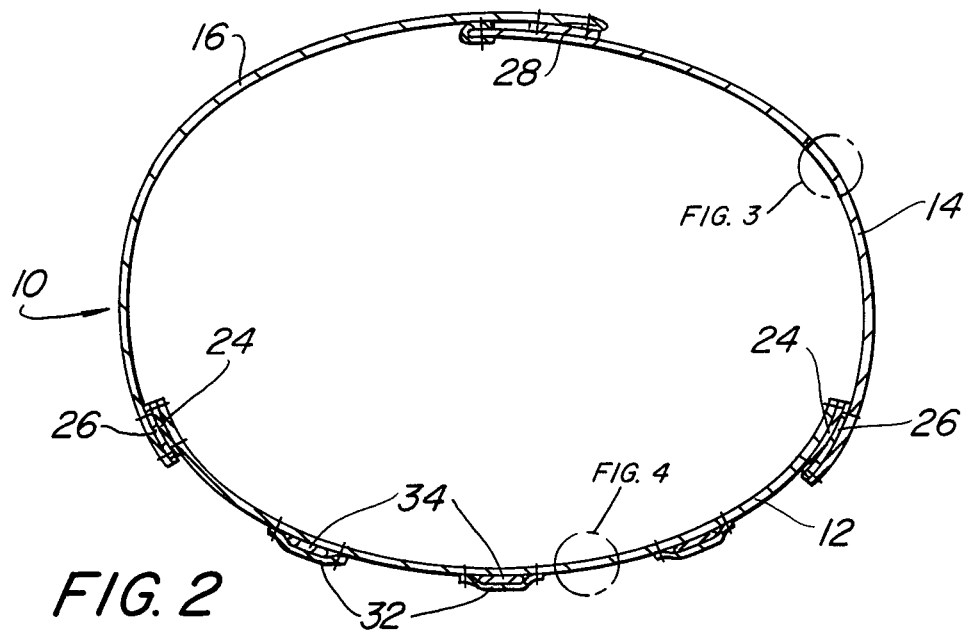

COLD COMPRESS

BACKGROUND OF THE INVENTION

The therapeutic effects of locally applied cold (cryotherapy) have been utilized by man for long periods of time. However, the mechanism of action has been poorly understood. Likewise, the use of compressive bandages has been known to control swelling and bleeding. All products currently available either rely on another device to apply compression with cold or fail to reach temperatures compatible with maximum therapeutic effects of cold, namely 0°-8° C. with 6° C. being the preferred temperature. An example of the former would include an icepack applied with an elastic bandage. An example of the latter includes gel bandages which rely on the latent heat of evaporation for skin cooling. Percutaneous electrical stimulation is known to relieve pain in certain cases. This invention also provides a means of incorporating stimulating electrodes into the bandage.

The present invention is directed to solution of the problem of a means for applying cold to an area of the body within a therapeutic range by way of an insulated, hygroscopic and protective material applied as a bandage.

SUMMARY OF THE INVENTION

The present invention is directed to a laminated bandage in the form of a layer of closed cell foam polymeric material sandwiched between and bonded to layers of fabric, said foam layer being substantially thicker than the layers of fabric. One of the layers of fabric is adapted to absorb water. A plurality of reinforcement pockets for stays are sewn on the other one of the layers of fabric. A plurality of straps are attached to one end of the bandage and adapted to be releasably engaged with mating structure on the other end of the bandage to secure the bandage in position against the body. A central pocket is provided for insertion of stays, supports or physical therapeutic agents.

Various objects and advantages of the present invention are set forth hereinafter.

For the purpose of illustrating the invention, there is shown in the drawings a form which is presently preferred; it being understood, however, that this invention is not limited to the precise arrangements and instrumentalities shown.

FIG. 1 is a perspective view of the compress of the present invention.

FIG. 2 is a sectional view taken along the line 2—2 in FIG. 1 with the straps attached to the bandage and on an enlarged scale.

FIG. 3 is an enlarged detail of a portion of the compress of FIG. 2.

FIG. 4 is an enlarged detail of another portion of the compress of FIG. 2.

DETAILED DESCRIPTION

Referring to the drawings, wherein like numerals indicate like elements, there is shown in FIGS. 1 and 2 a compress in accordance with the present invention designated generally as 10. The compress comprises three elements, a bandage 12, a panel 14, and a plurality of straps 16.

The bandage 12 is laminated and preferably comprises a layer of closed cell foam polymeric material 18 sandwiched between and bonded to layers of fabrics 20 and 22. See FIG. 4. Layer 18 may be substantially thicker than the layers 20 and 22. It is important that layer 18 be a closed cell layer. Layer 20, which is the layer adapted to be in contact with the skin, is an absorbent layer of towelling fabric such as terry cloth having longitudinal stretch. Layer 22 is preferably a woven layer of nylon or LYCRA (trademark) which is woven from spandex fibers having stretch in the longitudinal direction. Layer 22 preferably reflects cold that tends to escape through the closed cell layer back toward the terry cloth layer and slows the tendency of the bandage to warm to room temperature. The outer surface of layer 22 reflects heat and similarly slows the warming of the bandage.

By way of example and not by way of limitation, preferred thicknesses for the layers are as follows: layer 22 preferably has a thickness of 1/32", layer 18 preferably has a thickness of 3/16", and layer 20 preferably has a thickness of 1/16". Layers 20 and 22 are preferably bonded to layer 18 by application of heat and pressure. While layer 22 preferably has stretch in the longitudinal direction, it may optionally have stretch in both the longitudinal and transverse directions.

As shown in FIGS. 1 and 2, the bandage 12 is provided at opposite ends with a transverse panel 24 of VELCRO (trademark) material. Panel 24 may be stitched or otherwise fastened to the top surface of bandage 12. Each panel 24 is adapted to be releasably engaged with an associated mating transverse panel 26 of VELCRO material stitched or otherwise fastened to the end of panel 14 and the end of the plurality of straps 16.

A transverse panel 28 of VELCRO material is also stitched or otherwise secured to the other end of each of the straps 16. The transverse panels 28 are adapted to be releasably engaged with the top surface 30 of panel 14. As shown in detail in FIG. 3, substantially the entire top surface 30 may be made of a material adapted to mate with and releasably engage the transverse VELCRO panel 28 so as to facilitate adjustment. Thus, the straps 16 may be releasably secured at a variety of locations along top surface 30 according to the shape and waist size of the user.

It is an important feature that the element 16 comprise a plurality of elongated straps. For convenience, of applying the element 16 to the bandage 12, the plurality of straps may be stitched on otherwise fastened to the VELCRO panel 26 so that the plurality of straps may be secured to the bandage as a unit. Preferably, each of the straps 16 is made of an elastic material which can be stretched to enable placement of the individual straps at selected locations on the surface 30 of panel 14. In this way the compress can be made to conform to different shaped bodies as well as different waist sizes.

In use, the bandage 12 is removed from the panel 14 and straps 16, and soaked or dampened with water. It is necessary only for layer 20 to absorb water. Layer 18 will absorb a minor amount of water such as 5%. The bandage is then placed in a refrigerator and cooled to a temperature in the range of 0°-8° C. with the optimum temperature being approximately 6° C. Thereafter, the bandage is removed from the refrigerator and secured to panel 14 and straps 16 by engaging the VELCRO panels 24 of the bandage with the VELCRO panels 26 of the panel 14 and straps 16. The user places the bandage 12 on the injured area of the back and wraps the panel 14 about the waist while securing the straps 16 to the mating layer 30 at locations conforming to the user's waist size and body shape. Even though it contains ice crystals, the bandage 12 will conform to the area being treated, and will direct cold directly to that area.

Endorphins are released by the cold stimulus and by the application of pressure or electrical stimulation. The foam layer 18 is an insulator which minimizes heat transfer between inner and outer surfaces of the bandage 12. The layer 22 is preferably a light or reflective color so as to reflect heat away from the bandage. The bandage 12 is sufficiently pliable to anatomically conform to the back and will comform better as it warms up. The bandage 12 will gradually warm up to room temperature after about ½ hour.

For added support, a plurality of pockets 32 are stitched or otherwise fastened to the top layer 22 of the bandage 12, transversely of the compress. Elongated stays 34 may be inserted into the pockets to convert the compress into a brace. Physical therapeutic agents may be inserted into a central pocket.

The bandage can be modified for application to other parts of the body within the spirit and scope of the invention. Thus, smaller bandages could be made for application to the ankle or wrist of a user. The plurality of straps enables the compress to conform more readily to the various different body shapes. It is apparent that many modifications could be effected so that the bandage could be applied where needed.

The present invention may be embodied in other specific forms without departing from the spirit or essential attributes thereof and, accordingly, reference should be made to the appended claims, rather than to the foregoing specification, as indicating the scope of the invention.

I claim:

1. A compress comprising a bandage member and a strap element, said bandage member including an elongated layer of closed cell foam polymeric material sandwiched between and bonded to layers of fabric, one of said layers of fabric being absorbent with respect to aqueous liquids and adapted to be in contact with a body part and means at one end of the bandage member adapted to releasably engage with mating structure on the strap element, said strap element comprising a plurality of elongated elastic straps, one end of said straps being adapted to be secured to said bandage member and the other end of said straps having said mating structure.

2. A compress in accordance with claim 1, wherein the one end of each of the straps is secured to a panel, which panel is securable to the bandage member.

3. A compress in accordance with claim 2, wherein the strap element panel is adapted to be releasably engaged with mating structure on the bandage member.

4. A compress in accordance with claim 1, wherein the bandage member includes a bandage and a panel on the opposite end of the bandage from the strap element, the means at one end of the bandage member adapted to releasably engage the plurality of straps being a surface of said panel.

5. A compress in accordance with claim 4, wherein the bandage member panel is adapted to be releasably engaged with the bandage on the surface of the bandage opposite the absorbent fabric.

6. A compress in accordance with claim 1, wherein the elongated layer of foam material and the layers of fabric of the bandage member are stretchable in a longitudinal direction with respect to the length of the compress.

7. A compress in accordance with claim 6, wherein the one layer of fabric is the only layer which is readily absorbent.

8. A compress in accordance with claim 1, wherein the other layer of fabric is a light color for reflecting heat and cold.

9. A compress in accordance with claim 1, wherein the absorbent layer of fabric is terrycloth, and the other layer of fabric is stretchable in a longitudinal direction with respect to the length of the compress and has a light reflective color.

10. A compress in accordance with claim 1, wherein the foam layer is partially absorbent.

11. A compress in accordance with claim 1, wherein the bandage member includes a plurality of pockets on the fabric layer opposite the absorbent layer adapted to receive a plurality of elongated stays or physical therapeutic agents.

12. A compress comprising a bandage member and a strap element, said bandage member including an elongated layer of closed cell foam polymeric material sandwiched between and bonded to layers of fabric, one of said layers of fabric being absorbent with respect to aqueous liquids and adapted to be in contact with a body part, the other of said layers of fabric having a plurality of pockets adapted to receive a plurality of elongated stays, a means at one end of said bandage member adapted to releasably engage with mating structure to one end of said strap element, the end of said strap element opposite said one end with the mating structure being secured to the end of the bandage member opposite said one end of the bandage member with the mating structure, said strap element having a plurality of elongated elastic straps with the end opposite the end secured to said bandage member having said mating structure.

* * * * *